United States Patent
Kimura et al.

(10) Patent No.: US 8,808,192 B2
(45) Date of Patent: Aug. 19, 2014

(54) SIGNAL EXTRACTING APPARATUS

(75) Inventors: Yoshitaka Kimura, Sendai (JP); Nobuo Yaegashi, Sendai (JP); Mitsuyuki Nakao, Sendai (JP); Takuya Ito, Sendai (JP)

(73) Assignee: Tohoku University, Miyagi (JP)

( * ) Notice: Subject to any disclaimer, the term of this patent is extended or adjusted under 35 U.S.C. 154(b) by 101 days.

(21) Appl. No.: 13/496,586

(22) PCT Filed: Sep. 17, 2010

(86) PCT No.: PCT/JP2010/005687
§ 371 (c)(1),
(2), (4) Date: May 30, 2012

(87) PCT Pub. No.: WO2011/033784
PCT Pub. Date: Mar. 24, 2011

(65) Prior Publication Data
US 2012/0232418 A1    Sep. 13, 2012

(30) Foreign Application Priority Data

Sep. 18, 2009   (JP) ................ 2009-216716

(51) Int. Cl.
*A61B 5/02*   (2006.01)

(52) U.S. Cl.
USPC ........................................... 600/528

(58) Field of Classification Search
None
See application file for complete search history.

(56) References Cited

U.S. PATENT DOCUMENTS

| | | | |
|---|---|---|---|
| 2006/0161071 A1* | 7/2006 | Lynn et al. | 600/538 |
| 2006/0241510 A1* | 10/2006 | Halperin et al. | 600/534 |

FOREIGN PATENT DOCUMENTS

| | | |
|---|---|---|
| JP | 2006-204759 A | 8/2006 |
| JP | 2010-005000 A | 1/2010 |
| WO | 2009/110051 A1 | 9/2009 |

OTHER PUBLICATIONS

Broomhead, D.S. et al, Extracting Qualitative Dynamics From Experimental Data, Physica 20D (1986) pp. 217-236.
Jimenez-Gonzalez et al, Extracting Sources from noisy abdominal phonograms: a single-channel blind source separation method, Med Biol Eng Comput (2009) vol. 47, pp. 655-664.
Hataya, Toshiaki et al, A Simulation Studyh of Single-BSS with References, The Institute of Electronics, Information and Communication Engineers, MBB2009-68(Nov. 2009), vol. 109, No. 279, pp. 37-40.
Kimura Yoshitaka et al, Theoritical problems of the single-channel independent component analysis, BPES 2009.

* cited by examiner

*Primary Examiner* — Christopher D Koharski
*Assistant Examiner* — Elizabeth K So
(74) *Attorney, Agent, or Firm* — Bacon & Thomas, PLLC (57) ABSTRACT

A signal extracting apparatus is provided based on independent component analysis with reference for a single measured signal as a signal processing technique that allows stable and quick extraction of a target signal from single measured signal even in a high-noise environment with a high noise ratio against a target signal to be extracted. The signal extracting apparatus includes: a single-signal measuring unit to measure a measured signal as a single time-series signal containing a target signal obtained by measurement by a single channel; a reference signal creating unit (2) to create a reference signal provided with timing-axis information based on the time-series signal obtained by the single-signal measuring unit; and a main processing unit (5) to perform independent component analysis with reference for a single measured signal by capturing the reference signal obtained by the reference signal creating unit (2) and providing the timing-axis information for an algorithm in a reference system to extract an independent component.

20 Claims, 3 Drawing Sheets

SIGNAL EXTRACTING APPARATUS

BACKGROUND OF THE INVENTION

1. Field of the Invention

The present invention relates to the technique for extracting target signals from time-series signals, and more specifically, to signal extraction using the independent component analysis with reference.

2. Description of the Related Art

A conventional fetal phonocardiogram basically monitors faint pulses emanating from a fetal heart using a microphone placed on a maternal body surface, and therefore the measurement is limited to be conducted in a resting environment with lower ambient noises for only a short time period, so that the technique hardly gains the attention these days and is considered to be an insufficient technique. However, with the advantages such as the feasibility with very low cost and the high safeness because fetal heart sound is obtained outside of a maternal body, it may be made to an effective technique that can easily monitor a fetal condition at home if the technique is provided to enable long-term monitoring even in a high-noise environment.

Meanwhile, the independent component analysis has been established as a novel method of signal analysis that can extract target signals even in a high-noise environment where signals are feebler than noises. This is a method of signal analysis to separate signals based on a difference in probability distribution of the target signals using a plurality of measured signals, and offers incomparable characteristics that it can extract the target signals while preserving overall frequency components. In actual data, however, a measured signal may often be a single signal such as in the case of the fetal phonocardiogram, so that the development of independent component analysis for a single measured signal has been expected.

As the independent component analysis for a single measured signal, a method of embedding the measured signals in a time-delay coordinate system has been proposed (see Non-Patent Document 1 below).

This is the method of converting singular value decomposition in the time-delay coordinate system (see Non-Patent Document 2 below) to the independent component analysis. Specifically, given that measured data $x=(x_1, x_2, x_3, \ldots, x_N)$, m-dimensional data as described by Formula 1 is created using the time delay from x, and the singular value decomposition or the independent component analysis is conducted therefor to extract the target signals.

$$X = \begin{bmatrix} x_1, x_2, x_3, \ldots, x_n \\ x_{1-\tau}, x_{2-\tau}, x_{3-\tau}, \ldots, x_{n-\tau} \\ x_{1-2\tau}, x_{2-2\tau}, x_{3-2\tau}, \ldots, x_{n-2\tau} \\ \ldots \\ x_{1-(m-1)\tau}, x_{2-(m-1)\tau}, x_{3-(m-1)\tau}, \ldots, x_{n-(m-1)\tau} \end{bmatrix} \quad [\text{Formula 1}]$$

However, as disclosed in Non-Patent Document 3 below, this method has a disadvantage that the independent component analysis involves addition/subtraction within each row and therefore the mixture of time is caused, leading to randomness in time coordinates of the obtained analysis results. Although various attempts have been made to overcome this problem, a fundamental solution has not been found.

As disclosed in Patent Document 1 below, for example, the inventors of the present invention have been studied on the independent component analysis with reference for searching target signals based on reference signals in the independent component analysis.

PRIOR ART DOCUMENT

Patent Document 1: JP 2006-204759 A
Non-Patent Document 1: A. Jimenez-Gonzalez and C. J. James, "Extracting sources from noisy abdominal phonograms: a single-channel blind source separation method", Med Biol Eng Comput, Vol. 47, pp. 655-664 (2009)
Non-Patent Document 2: D. S. Broomhead and Gregory P. King, "Extracting Qualitative Dynamics from Experimental Data", Physica D, Vol. 20, pp. 217-236 (1986)
Non-Patent Document 3: Yoshitaka KIMURA, Toshiaki HATAYA, Takuya ITO, Hiroshi TISAKA, Nobuo YAEGASHI, Mitsuyuki NAKAO, "Theoretical problems of the single-channel independent component analysis", Proceedings of the 24th Symposium on Biological and Physiological Engineering (2009)

SUMMARY OF THE INVENTION

As described above, there has been a problem in that the conventional analysis of fetal heart sound signals does not allow stable monitoring in a high-noise environment. In addition, independent component separation from a single measured signal was impossible.

The present invention is directed to provide the extraction of target signals from a limited number of time-series signals.

In one aspect, a signal extracting apparatus of the present invention includes: a signal input unit to input one or more time-series signals in which elements are arranged in temporal order; a generating unit to generate a plurality of short time-series signals by selecting the elements from the time-series signals, wherein at least one time-series signal generates two or more short time-series signals wherein the selected elements have different but partially overlapping temporal ranges with each other; a reference signal creating unit to create a reference signal indicating a temporal characteristic of an independent signal to be extracted; and an independent component analysis with reference (ICA-R) unit to perform independent component analysis with reference for a plurality of the short time-series signals generated by the generating unit based on the reference signal to extract the independent signal.

The signal extracting apparatus is constructed using computer hardware with a memory device or a processing unit (in many cases, also with an input device, an output device, or the like). The computer hardware may be constructed by a single device or a plurality of devices communicable with each other. This computer hardware achieves the signal extraction processing in many cases by causing the processing unit to execute a computer program (software) which is to be stored in the memory device, so as to control data communication between the memory device and the processing unit or data processing by the processing unit. The signal extraction processing can also be performed by implementing a portion of a signal extraction circuit or the entire circuit in a hardware form in the computer hardware.

The signal input unit inputs the time-series signals. Typically, the input time-series signals are stored in the memory device. Although it is possible to use temporally continuous analog signals (analog data) as the time-series signals (time-series data), it is desirable to use temporally discrete digital signals (digital data) in consideration of easiness of the signal processing. The time-series signals are those containing a plurality of temporal elements, where the respective elements are arranged in temporal order by storing them in temporal order or relating them to time. There are one or more time-series signals to be input. An example where a plurality of signals are input includes an aspect to input one or more time-series signals considered to contain a sufficient number of target signals, or an aspect to use the time-series signals considered to contain a sufficient level of noises that are desirably removed from these time-series signals.

The generating unit is a configuration to pre-process the signals prior to the processing of the independent component analysis with reference. The generating unit generates a plurality of time-series signals in a short temporal range (referred to as the short time-series signals) from the time-series signals. Although all the elements in the temporal range may be taken out in generating the short time-series signals, the elements may be discretely taken out in accordance with a setup rule. The processing of the generating unit includes generation of two or more short time-series signals where the selected elements have different but partially overlapping temporal ranges with each other. This processing is performed, for example, by shifting the temporal ranges (e.g. from T1 to T2) of the elements to be selected by a certain time interval $\Delta T$ (i.e. by selecting specific short time-series signals from the elements contained in the temporal range of time T1 to T2, selecting the second short time-series signals from the elements contained in the temporal range of T1+$\Delta T$ to T2+$\Delta T$, and selecting the third short time-series signals from the elements contained in the temporal range of T1+2$\Delta T$ to T2+2$\Delta T$).

The reference signal creating unit creates the reference signal indicating the temporal characteristic of the independent signal to be extracted. An example of the temporal characteristic can include timing when peak or zero value appears, a shape of the peak, a pattern having appropriate frequency or a frequency band, and the like.

The ICA-R unit performs the independent component analysis with reference for a plurality of the short time-series signals generated by the generating unit, based on the reference signal to extract the independent signal. The independent component analysis is the analysis to evaluate a certain independency between the signals (e.g. statistical independency) and extract a plurality of independent signals (which are also the time-series signals). In addition, the independent component analysis with reference is, upon extracting the independent signals, to define the characteristics to which one or more independent signals should correspond through the reference signals. Various ways of defining the characteristics are possible, including an aspect to define a threshold that should be exceeded by a degree of correlation between a reference signal and an independent signal. Typically, a plurality of independent signals to be extracted are partially or wholly stored or output, and utilized in the analysis of computer users or the like.

The operation of this signal extracting apparatus corresponds to the generation of a plurality of short time-series signals (which can be considered to be measured data derived from a pseudo multichannel) from the input time-series signals to perform the independent component analysis with reference. As such, more number of the independent signals than the number of initially input time-series signals can be separated and extracted. Although a plurality of short time-series signals temporally overlap with each other, the temporal characteristics of the independent signals can be understood because part or all of these signals are extracted utilizing the characteristics in the timing-axis direction based on the reference signals. That is, while in the standard independent component analysis the columns may be interchanged and the timing at which each independent component is extracted may vary due to the extraction results of the independent components, in the independent component analysis with reference the independent components are extracted based on the reference signals and thus the mixture of time can be reduced.

In an aspect of the signal extracting apparatus of the present invention, the independent signal to be extracted contains a signal that is considered to be autoregressive, and the generating unit generates a plurality of the short time-series signals having different but partially overlapping temporal ranges so that one or more short time-series signals are dependent on one or more other short time-series signals when interpreted based on the autoregressive relationship.

Autoregressive means that a value of a signal at certain time can be described linearly using a value of the signal at certain previous time. In other words, a value of a signal at certain time can be described linearly using a value of the signal at certain following time. In addition, a constant term or an error term may be contained therein. The signals considered to be autoregressive are not required to be describable as an autoregressive model in a mathematically strict sense, and it may be sufficient to be the autoregressive model in an approximate sense. Types of signals that are analyzed by applying the autoregressive model would often be regarded to be autoregressive. If such an autoregressive characteristic is provided and more short time-series signals are created than the number of orders of autoregression (the number of timings to be dependent), these signals present dependent information. As illustrated in the embodiments, however, the independent component analysis can be performed in such cases as well.

In an aspect of the signal extracting apparatus of the present invention, the generating unit generates m short time-series signals having n elements to generate a matrix X of elements n×m, and the ICA-R unit performs the independent component analysis with reference for the matrix X to calculate an independent component matrix Y of elements m×n having a plurality of independent signals as the elements and a matrix W of elements m×m in a matrix algebra relationship of Y=WX.

In an aspect of the signal extracting apparatus of the present invention, a single time-series signal is input by the signal input unit. According to this aspect, when only a single time-series signal obtained by a single sensor is input, a plurality of independent signals contained in the time-series signal can also be extracted.

In an aspect of the signal extracting apparatus of the present invention, the reference signal creating unit uses a temporal filter to generate, from the time-series signal, the reference signal indicating the temporal characteristics of the independent component to be extracted.

In an aspect of the signal extracting apparatus of the present invention, the time-series signal is obtained by diagnosis of a living body, and the independent signal to be extracted includes a biosignal.

In an aspect of the signal extracting apparatus of the present invention, the independent signal to be extracted includes a signal regarding fetal heart sound.

In the present invention, any of the aspects [1] to [9] below is also possible.

[1] A signal extracting apparatus including: a single-signal input unit to input a single time-series signal; a reference signal creating unit to create a reference signal; and a main processing unit to perform independent component analysis with reference for a single measured signal by capturing the reference signal obtained by the reference signal creating unit and providing timing-axis information for an algorithm in a reference system to extract an independent component.

[2] The signal extracting apparatus according to [1] above including a separation matrix initial value processing unit that identifies an output signal obtained by the main processing unit to allow the subsequent analyses to be performed in a shorter time period.

[3] The signal extracting apparatus according to [1] above, wherein the reference signal creating unit creates one or more reference signals preserving temporal information from the time-series signal obtained by the single-signal input unit using one or more band-pass filters.

[4] The signal extracting apparatus according to [3] above, wherein the main processing unit includes an embedding dimensional space generating unit to generate an embedding dimensional space made from time delay from the time-series signal obtained by the single-signal input unit and an independent component analysis with reference (ICA-R) unit to perform independent component analysis with reference by capturing the reference signal obtained by the reference signal creating unit.

[5] The signal extracting apparatus according to [4] above, wherein the embedding dimensional space generating unit extracts, from the time-series signals of which the time-series starts at the present time, time-series before 1–n at a τ time interval, then extracts similarly the time-series before 1–n that starts at point back to τ time before, subsequently extracts similarly the time-series before 1–n that starts at the point back to 2τ time before, and further subsequently extracts the time-series before 1–n that starts at the point back to MT time before to generate a matrix X of m×n having these time-series as row vectors.

[6] The signal extracting apparatus according to [5] above, wherein the main processing unit uses the reference signal obtained by the reference signal creating unit to calculate an independent component matrix Y of m×n and a matrix W of m×m that extracts the independent component from the matrix X by the independent component analysis with reference.

[7] The signal extracting apparatus according to [1] above, wherein the time-series signal is a biosignal.

[8] The signal extracting apparatus according to [7] above, wherein the target signal extracted from the biosignal is fetal heart sound.

[9] The signal extracting apparatus according to [7] above, wherein the target signal extracted from the biosignal is maternal heart sound, a maternal breathing component, a fetal breathing component, fetal electrocardiogram, maternal electrocardiogram, or maternal electromyogram.

Each aspect of the present invention can be described as the invention of a method of performing each processing, the invention of a program to cause a computer to perform the processing for each step, or the invention of a storage medium in which the program is recorded.

Effects of the Invention

According to the present invention, target signals can be extracted properly from one or more measured signals even in a high-noise environment.

Also, when applied to fetal monitoring, it can provide a fetal heart sound extracting apparatus which is able to stably separate fetal heart sound.

DESCRIPTION OF THE EMBODIMENTS

A signal extracting apparatus according to the present invention is characterized by including: a single-signal measuring unit to measure a measured signal as a single time-series signal containing a target signal obtained by measurement by a single channel; a reference signal creating unit to create a reference signal from the measured signal obtained by the single-signal measuring unit; a central processing unit; a memory device connected to the central processing unit; and a main processing unit to perform independent component analysis with reference for a single measured signal by capturing the reference signal obtained by the reference signal creating unit and providing timing-axis information to the measured signal in a reference system to extract an independent component.

Embodiments

Hereinbelow, embodiments of the present invention will be described in reference to the drawings.

Figure 1:
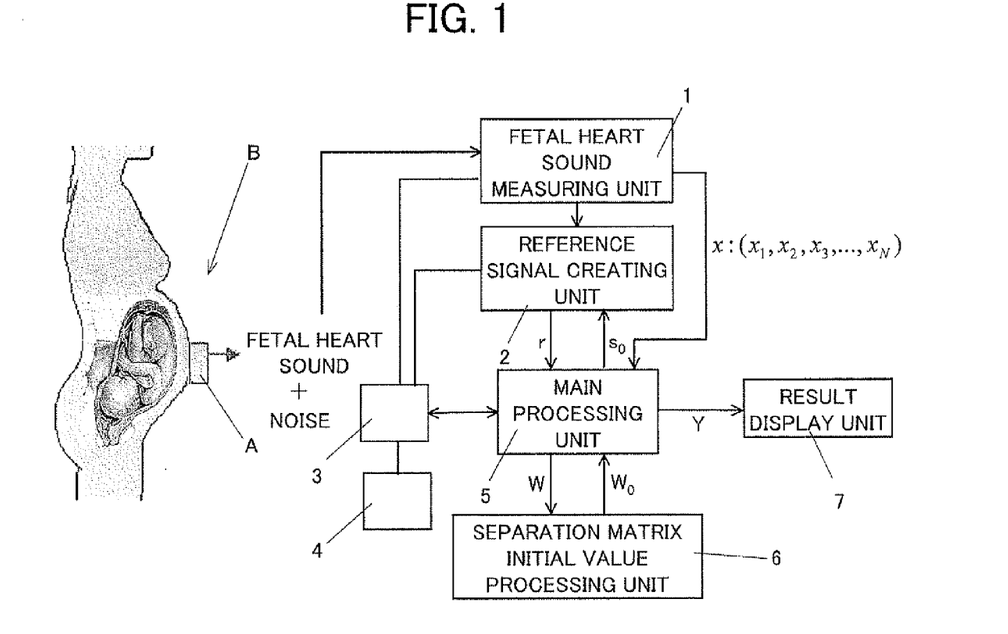
FIG. 1 shows a schematic block diagram of a fetal heart sound extracting apparatus illustrating an embodiment of the present invention.
Figure 2:
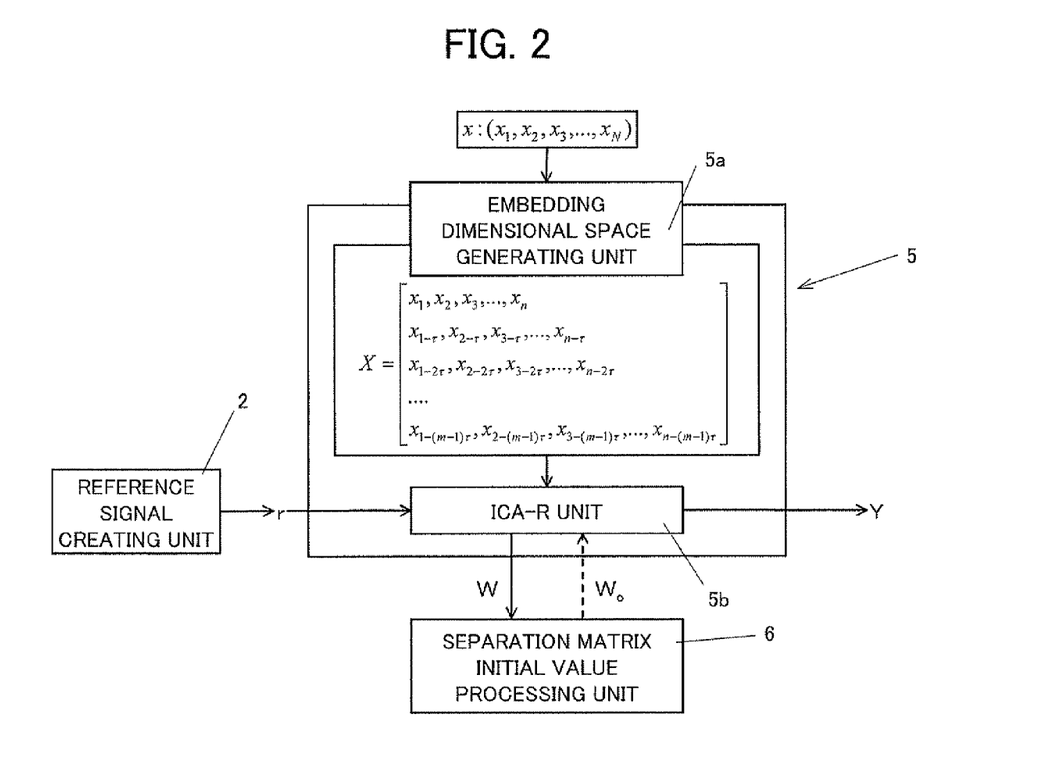
FIG. 2 shows a schematic block diagram of a main processing unit of the fetal heart sound extracting apparatus illustrating an embodiment of the present invention.

FIG. 1 shows a schematic block diagram of a fetal heart sound extracting apparatus illustrating an embodiment of the present invention, and FIG. 2 shows a schematic block diagram of a main processing unit of the fetal heart sound extracting apparatus.

In FIG. 1, reference numeral 1 denotes a fetal heart sound measuring unit to measure biosignals. Measured signals (x: $x_1, x_2, x_3, \ldots, x_N$) obtained by a measuring apparatus placed on a body surface of a maternal body B conceiving a fetal A is input to a reference signal creating unit 2 which generates signals obtained through a frequency band-pass filter of a frequency band containing as many target signals as possible in order to extract the target signals, or signals such as functions of timing at which the target signals are produced as reference signals r in order to extract periodic signals such as fetal phonocardiogram. Here the reference signals r are created while a timing-axis is set to the present time. The apparatus in FIG. 1 is also provided with a central processing unit 3, and a memory device 4 connected to the central processing unit 3 and embedded with read only memory (ROM) for writing an operating program or reference values of computation results or random access memory (RAM) for storing various data. There are further provided a main processing unit 5, a separation matrix initial value processing unit 6, and a result display unit 7 of the main processing unit 5. The main processing unit 5 is configured to output an output signal $S_0$ and return the signal back to the reference signal creating unit 2, so as to confirm if the delay time is not shifted. In these figures, input and output ports of the respective units are omitted.

Next, in FIG. 2, the main processing unit 5 includes an embedding dimensional space generating unit 5a to generate multi-dimensional time-series, and an independent component analysis with reference (ICA-R) unit 5b for performing the independent component analysis with reference to compute a separation matrix W and independent component time-series Y from an initial matrix $W_0$ obtained by the separation matrix initial value processing unit 6. The separation matrix W calculated at this point is input to the separation matrix initial value processing unit 6, and if a correlation coefficient between the independent component time-series Y and the reference signal r of the target signal such as the fetal heart sound is 0.7 or above, then input to the ICA-R unit 5b of the main processing unit 5 as the initial matrix $W_0$ for iterative estimation used in the main processing unit 5. The correlation coefficient mentioned above is an arbitrary unit and ranges from −1 to 1.

Now, the principle to extract the signals in an embedding dimension N according to the single-signal independent component analysis for a single signal of the present invention will be described. That is, a method of separating the signals with different model orders containing noise signals when the autoregressive model is created by the autoregressive (AR) model method will be described.

$$\vec{x}_n = (x_n, x_{n+1}, x_{n+2}, \ldots, x_{n+N-1}) = \alpha \vec{S}_n^{\,1} + \beta \vec{S}_n^{\,2}$$

$$\vec{S}_n^{\,i} = (S_n^i, S_{n+1}^i, S_{n+2}^i, \ldots, S_{n+N-1}^i)(i=1,2) \quad \text{[Formula 2]}$$

Here, $\vec{x}_n$ is measured data from time n to time n+N−1 as described by Formula 2. Also, $S_n^1$ is independent components intended for the extraction, $S_n^2$ is other independent components, and α and β are mixing ratios of these independent components.

Now, consider the matrix X as described by Formula 3 formed by the measured signals in the embedding space (embedding dimension N).

$$X = \begin{pmatrix} \vec{x}_n \\ \vec{x}_{n-1} \\ \ldots \\ \vec{x}_{n-m+2} \\ \vec{x}_{n-m+1} \end{pmatrix} \quad \text{[Formula 3]}$$

Assumed that all the target signals are autoregressive (general Markov signals) and the order of each independent component including the noise components is different from each other. The number of measured data having the embedding dimension N to be prepared must be equal or more than the product of the order of the autoregressive model (the number of elements at other timings than the time at which the elements are described) and the number of independent components to be extracted. For example, if the order of the autoregressive model of the target signal is the fourth order and three target signals including the noise are to be separated, the required number of measured data would be 12. Hereafter, the explanation is made assuming that the order of the target signals is the fourth order for simplicity of explanation. Assuming that it can be described by $$S_{n-4}^i = (a_1^i, a_2^i, a_3^i, a_4^i) \begin{pmatrix} S_n^i \\ S_{n-1}^i \\ S_{n-2}^i \\ S_{n-3}^i \end{pmatrix}$$

Here, a factor to specify the timing can be inserted.

Then, using a companion matrix A as described by Formula 4, $S_{n-4-L}^i$ (L=1, 2, . . . , n−4−(m−N−4)) is described as Formula 5 using a noise term $S_n^i, S_{n-1}^i, S_{n-2}^i, S_{n-3}^i$.

$$A = \begin{pmatrix} 0, 1, 0, 0 \\ 0, 0, 1, 0 \\ 0, 0, 0, 1 \\ a_1^i, a_2^i, a_3^i, a_4^i \end{pmatrix} \quad \text{[Formula 4]}$$

$$S_{n-4-L}^i = (a_1^i, a_2^i, a_3^i, a_4^i) A^L \begin{pmatrix} S_n^i \\ S_{n-1}^i \\ S_{n-2}^i \\ S_{n-3}^i \end{pmatrix} + \quad \text{[Formula 5]}$$

$$\sum_{i=1}^{L} (a_1^i, a_2^i, a_3^i, a_4^i) A^{L-1} \begin{pmatrix} 0 \\ 0 \\ 0 \\ N_{n-l+1}^i \end{pmatrix} + N_{n-L}^i$$

If Formula 5 is applied to each column of n−4−1 and thereafter of the matrix X, the formula is similarly effective for different orders as well when i=2. Thus, the mixing ratio of the true independent components (here, $S_n^i, S_{n-}^i, S_{n-2}^i, S_{n-3}^i$) of each column of n−4−1 and thereafter of the matrix X varies in each column.

Therefore, each column contains independent information and thus the target signals can be extracted successively using the independent component analysis for Y=WX, as shown in FIG. 2.

According to the present invention, the timing-axis information is provided for an algorithm in a reference system, so that the independent components are extracted in combination therewith and the mixture of time can be reduced in the independent component analysis with reference.

Referring again to FIGS. 1 and 2, the ICA-R unit 5b uses the iterative estimation to estimate the separation matrix W to separate the signals into the independent components by the independent component analysis with reference. At this point, a unit matrix is usually used as the initial matrix $W_0$. However, there is an advantage that, after the same computation is performed using another data, using the separation matrix W as the result of the same processing performed previously instead of using the unit matrix as the initial matrix $W_0$ can accelerate the convergence of the iterative estimation (for example, the time period can be reduced to approximately one-third for the iterative estimation), so that such a manner of iteration is utilized.

The separation matrix initial value processing unit 6 verifies whether the separation matrix W as the result of the same processing performed previously and stored in the memory device 4 is effective as the separation matrix, based on the degree of the correlation coefficient, then determines if the separation of the fetal heart sound is possible to a certain degree when the separation matrix W is applied to the matrix X of m×n obtained using the time delay from the measured signal x. If the correlation coefficient between the separation matrix W and the reference signal equals to or greater than a given value (e.g. 0.7), the matrix is returned as the initial matrix $W_0$ to the ICA-R unit 5b of the main processing unit 5 to perform the independent component analysis with reference. That is, in the case where the signals obtained by the main processing unit 5 are identified and the analysis is performed iteratively, the main processing unit 5 receives the return signals that serve to cut down the time period of analysis compared to the previous analysis.

Figure 3:
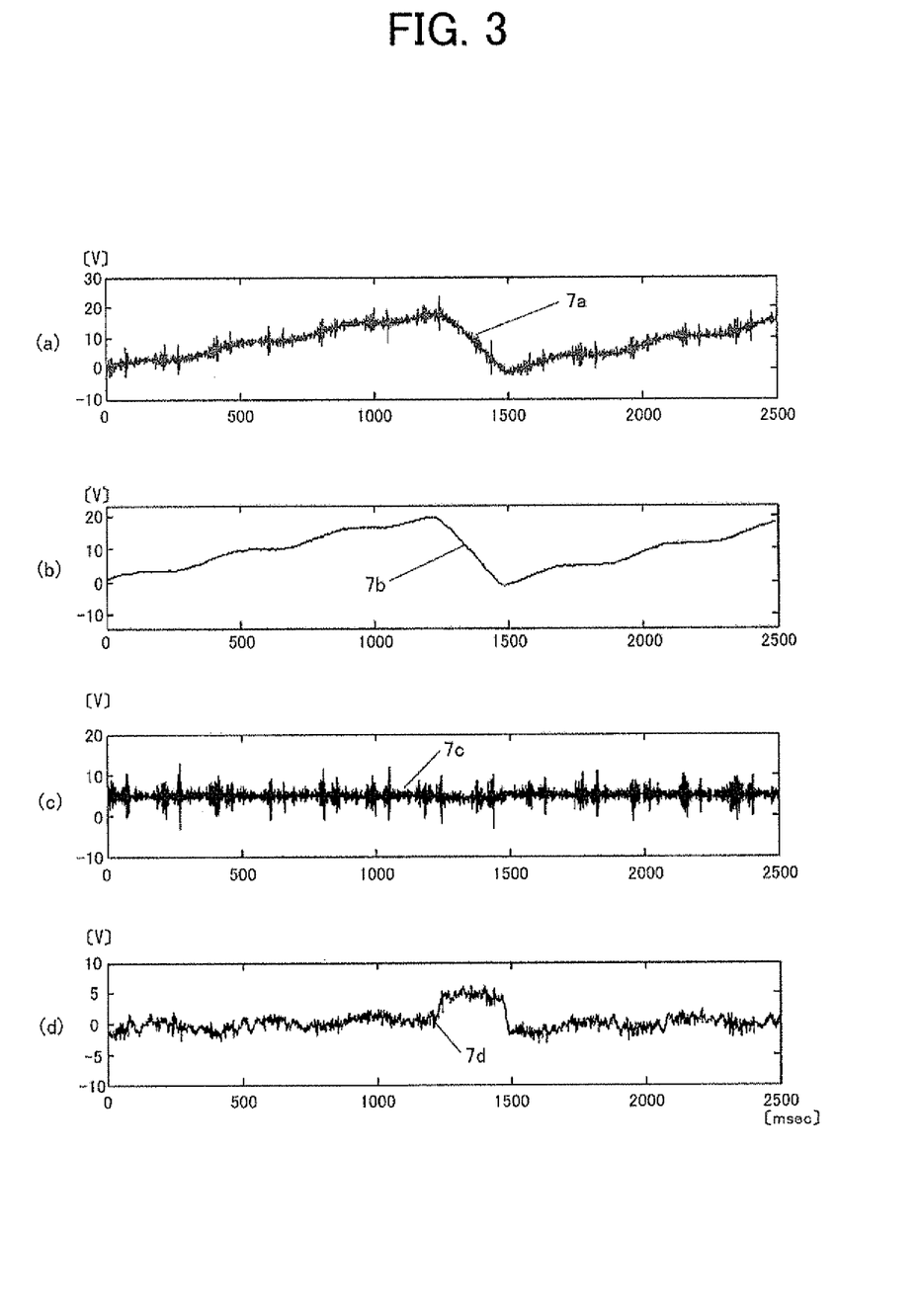
FIG. 3 shows a graph of an example in which fetal heart sound data is actually analyzed from phonocardiogram data, illustrating an embodiment of the present invention.

FIG. 3 shows a graph of an example in which fetal heart sound data is actually analyzed from phonocardiogram data illustrating an embodiment of the present invention. In this figure, FIG. 3(a) shows a measured signal, FIG. 3(b) shows a fluctuation component of maternal breathing, FIG. 3(c) shows a fetal heart sound component, and FIG. 3(d) shows a fetal breathing component.

It can be seen that a fluctuation component of maternal breathing 7b, a fetal heart sound component 7c, and a fetal breathing component 7d are separated properly from each other. It can also be seen that, when considering a descending section (expiration section) of the fluctuation component of maternal breathing 7b, timing deviation among the respective independent components is not found unlike the case disclosed in Non-Patent Document 1, and the independent components are extracted while preserving the temporal consistency. In this example, the reference signal is created under the condition that the embedding dimension is a 30th dimension and the delay time $\tau$ is 1 ms, using the matrix $W_0$ as a 30th-order unit square matrix and band-pass filters of frequencies of 0.1 to 1 Hz, 1 to 5 Hz, and 100 to 498 Hz.

This analysis is effective in any signal analyses other than the fetal heart sound analysis. In particular, it is suitable for separation of nonlinear time-series, such as chaos and a fractal signal. It is also effective in the case where noises are higher than signals.

Figure 4:
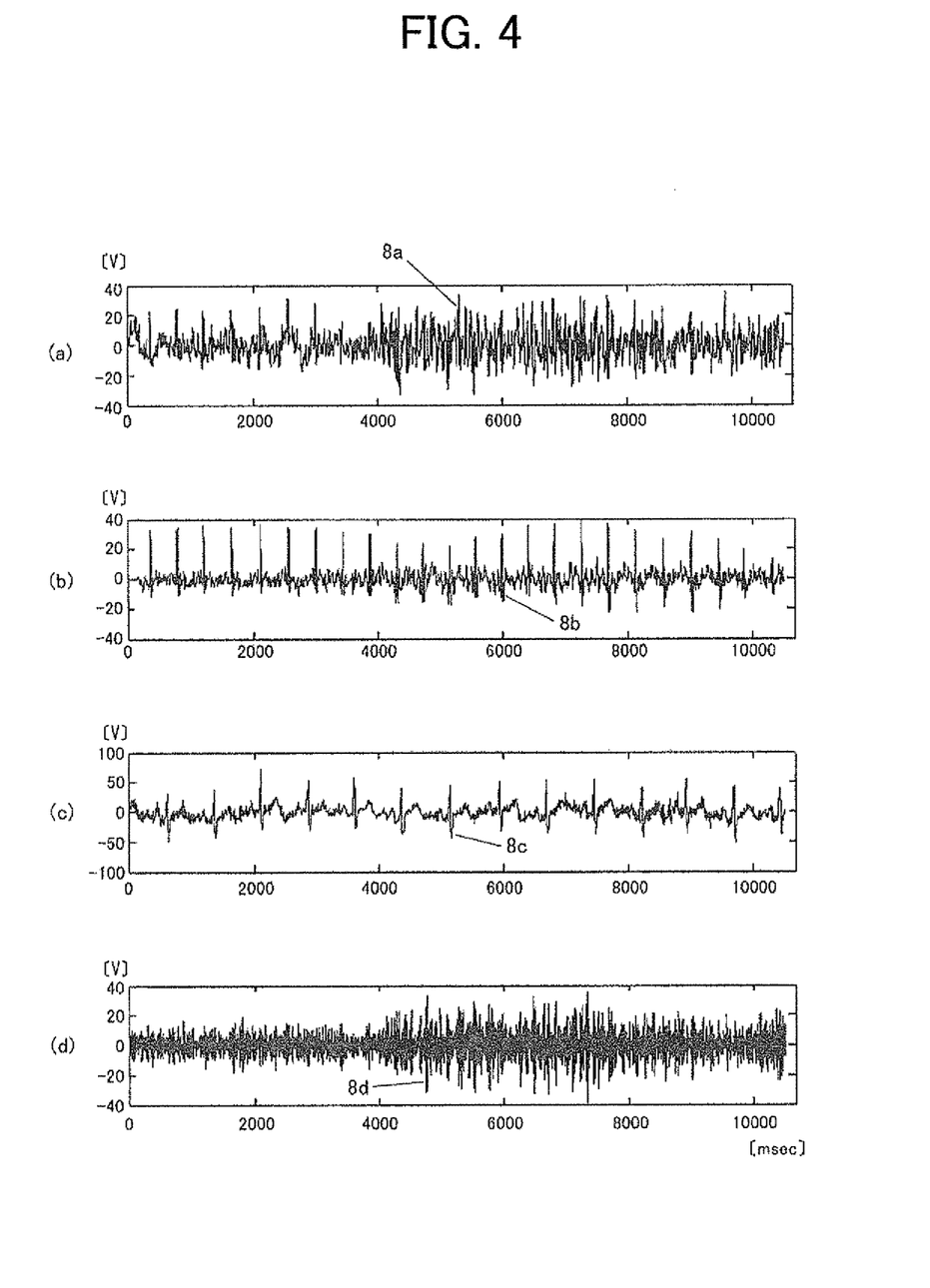
FIG. 4 shows a graph of an example in which maternal electromyogram is separated from electrocardiogram data, illustrating an embodiment of the present invention.

FIG. 4 shows a graph of an example in which a maternal electromyogram is separated from electrocardiogram data. In FIG. 4(a), a measured signal 8a contains a large amount of electromyogram components in the later part, concealing the most amount of fetal electrocardiogram components. FIG. 4(b) shows an extracted fetal electrocardiogram component 8b, FIG. 4(c) shows a maternal electrocardiogram component 8c, and FIG. 4(d) shows a maternal electromyogram component ed. It can be found from these figures that the fetal electrocardiogram component 8b can be extracted, which is mostly concealed by the maternal electromyogram component 8d. In this example, the reference signal is created under the condition that the embedding dimension is a 12th dimension, the delay time $\tau$ is 1 ms, and the sampling time period is 5000 ms, using the band-pass filters (temporal filters) of frequencies of 1 Hz and lower, 1 to 70 Hz, and 70 Hz and higher.

As described above, the present invention is applicable to various fields such as analysis of fetal heart sound data, separation of maternal electromyogram from electrocardiogram data, and the like.

In addition, the fetal heart sound extracting apparatus of the present invention can be utilized broadly as an inexpensive portable fetal monitoring apparatus.

Although the embodiments above are described mainly in terms of the fetal heart sound extracting apparatus, the present invention is not limited thereto and applicable to the following as well.

(1) Neural function analysis by separation of neural pulses;
(2) Biological function analysis based on fluctuation analysis of fluctuation in cardiac rate or blood pressure;
(3) Cellular function estimation based on fluctuation analysis of measured signals of single-molecule movement;
(4) Method of removing noises for picked-up images obtained by a solid-state imaging sensor such as CCD and CMOS;
(5) Method of removing noises for a television set such as a satellite television set;
(6) Method of removing noises for a recording/reproducing apparatus of video signals or audio signals;
(7) Method of removing noise components from transmission signals for various digital circuits such as a plant control apparatus; and
(8) Method of removing noise components in signals obtained from various sensors such as an optical sensor, a magnetic sensor, and a gas sensor.

INDUSTRIAL APPLICABILITY

The target signal extracting apparatus of the present invention is applicable, for example, as a tool that allows proper extraction of target signals even when applied for fetal heart sound containing high noises as compared to the target signals.

What is claimed is:

1. A signal extracting apparatus, comprising:
a signal input unit to input one or more time-series signals in which elements are arranged in temporal order;
a generating unit to generate a plurality of short time-series signals by selecting the elements from the time-series signals, wherein at least one time-series signal generates two or more short time-series signals where the selected elements have different but partially overlapping temporal ranges with each other;
a reference signal creating unit to create a reference signal indicating a temporal characteristic of an independent signal to be extracted; and
an independent component analysis with reference (ICA-R) unit to perform independent component analysis with reference for a plurality of the short time-series signals generated by the generating unit based on the reference signal to extract the independent signal,
wherein the independent signal to be extracted contains a signal that is considered to be autoregressive, and
the generating unit generates a plurality of the short time-series signals having different but partially overlapping temporal ranges so that one or more short time-series signals are dependent on one or more other short time-series signals when interpreted based on the autoregressive relationship.

2. The signal extracting apparatus according to claim 1, wherein a single time-series signal is input by the signal input unit.

3. The signal extracting apparatus according to claim 1, wherein the reference signal creating unit uses a temporal filter to generate, from the time-series signal, the reference signal indicating the temporal characteristics of the independent component to be extracted.

4. The signal extracting apparatus according to claim 1, wherein the time-series signal is obtained by diagnosis of a living body, and the independent signal to be extracted includes a biosignal.

5. The signal extracting apparatus according to claim 4, wherein the independent signal to be extracted includes a signal regarding fetal heart sound.

6. A signal extracting apparatus, comprising:
(a) a single-signal input unit to input a single time-series signal;
(b) a reference signal creating unit to create a reference signal; and
(c) a main processing unit to perform independent component analysis with reference for a single measured signal by capturing the reference signal obtained by the reference signal creating unit and providing timing-axis information for an algorithm in a reference system to extract an independent component.

7. The signal extracting apparatus according to claim 6, wherein the independent signal to be extracted includes a signal regarding fetal heart sound.

8. A signal extracting program for a computer, comprising the steps of:
  inputting one or more time-series signals in which elements are arranged in temporal order;
  generating a plurality of short time-series signals by selecting the elements from the time-series signals, wherein at least one time-series signal generates two or more short time-series signals where the selected elements have different but partially overlapping temporal ranges with each other;
  creating a reference signal indicating a temporal characteristic of an independent signal to be extracted; and
  performing independent component analysis with reference for a plurality of the short time-series signals generated at the generating step based on the reference signal to extract the independent signal,
  wherein the independent signal to be extracted contains a signal that is considered to be autoregressive, and
  the generating unit generates a plurality of the short time-series signals having different but partially overlapping temporal ranges so that one or more short time-series signals are dependent on one or more other short time-series signals when interpreted based on the autoregressive relationship.

9. The signal extracting program according to claim 8, wherein the independent signal to be extracted includes a signal regarding fetal heart sound.

10. A signal extracting method for a computer, comprising the steps of:
  inputting one or more time-series signals in which elements are arranged in temporal order;
  generating a plurality of short time-series signals by selecting the elements from the time-series signals, wherein at least one time-series signal generates two or more short time-series signals where the selected elements have different but partially overlapping temporal ranges with each other;
  creating a reference signal indicating a temporal characteristic of an independent signal to be extracted; and
  performing independent component analysis with reference for a plurality of the short time-series signals generated at the generating step based on the reference signal to extract the independent signal,
  wherein the independent signal to be extracted contains a signal that is considered to be autoregressive, and
  the generating step generates a plurality of the short time-series signals having different but partially overlapping temporal ranges so that one or more short time-series signals are dependent on one or more other short time-series signals when interpreted based on the autoregressive relationship.

11. The signal extracting method according to claim 10, wherein the independent signal to be extracted includes a signal regarding fetal heart sound.

12. A signal extracting apparatus, comprising:
  a signal input unit to input one or more time-series signals in which elements are arranged in temporal order;
  a generating unit to generate a plurality of short time-series signals by selecting the elements from the time-series signals, wherein at least one time-series signal generates two or more short time-series signals where the selected elements have different but partially overlapping temporal ranges with each other;
  a reference signal creating unit to create a reference signal indicating a temporal characteristic of an independent signal to be extracted; and
  an independent component analysis with reference (ICA-R) unit to perform independent component analysis with reference for a plurality of the short time-series signals generated by the generating unit based on the reference signal to extract the independent signal,
  wherein the generating step generates m short time-series signals having n elements to generate a matrix X of elements n×m, and
  the ICA-R unit performs the independent component analysis with reference for the matrix X to calculate an independent component matrix Y of elements m×n having a plurality of independent signals as the elements and a matrix W of elements m×m in a matrix algebra relationship of Y=WX.

13. The signal extracting apparatus according to claim 12, wherein the a single time-series signal is input by the signal input unit.

14. The signal extracting apparatus according to claim 12, wherein the reference signal creating unit uses a temporal filter to generate, from the time-series signal, the reference signal indicating the temporal characteristics of the independent component to be extracted.

15. The signal extracting apparatus according to claim 12, wherein the time-series signal is obtained by diagnosis of a living body, and the independent signal to be extracted includes a biosignal.

16. The signal extracting apparatus according to claim 15, wherein the independent signal to be extracted includes a signal regarding fetal heart sound.

17. A signal extracting program for a computer, comprising the steps of:
  inputting one or more time-series signals in which elements are arranged in temporal order;
    generating a plurality of short time-series signals by selecting the elements from the time-series signals, wherein at least one time-series signal generates two or more short time-series signals where the selected elements have different but partially overlapping temporal ranges with each other;
    creating a reference signal indicating a temporal characteristic of an independent signal to be extracted; and
    performing independent component analysis with reference (ICA-R) for a plurality of the short time-series signals generated at the generating step based on the reference signal to extract the independent signal,
    wherein the generating step generates m short time-series signals having n elements to generate a matrix X of elements n×m, and
    the ICA-R performing step performs the independent component analysis with reference for the matrix X to calculate an independent component matrix Y of elements m×n having a plurality of independent signals as the elements and a matrix W of elements m×m in a matrix algebra relationship of Y=WX.

18. The signal extracting program according to claim 17, wherein the independent signal to be extracted includes a signal regarding fetal heart sound.

19. A signal extracting method for a computer, comprising the steps of:
  inputting one or more time-series signals in which elements are arranged in temporal order;
  generating a plurality of short time-series signals by selecting the elements from the time-series signals, wherein at least one time-series signal generates two or more short time-series signals where the selected elements have different but partially overlapping temporal ranges with each other;

creating a reference signal indicating a temporal characteristic of an independent signal to be extracted; and performing independent component analysis with reference (ICA-R) for a plurality of the short time-series signals generated at the generating step based on the reference signal to extract the independent signal, wherein the generating step generates m short time-series signals having n elements to generate a matrix X of elements n×m, and the ICA-R performing step performs the independent component analysis with reference for the matrix X to calculate an independent component matrix Y of elements m×n having a plurality of independent signals as the elements and a matrix W of elements m×m in a matrix algebra relationship of Y=WX.

20. The signal extracting method according to claim 19, wherein the independent signal to be extracted includes a signal regarding fetal heart sound.

* * * * *